US011229791B2

(12) United States Patent
Fan et al.

(10) Patent No.: US 11,229,791 B2
(45) Date of Patent: Jan. 25, 2022

(54) BEAUTY INSTRUMENT WITH MASK

(71) Applicant: Beijing FUNATE Innovation Technology Co., LTD., Beijing (CN)

(72) Inventors: Li Fan, Beijing (CN); Li Qian, Beijing (CN); Yu-Quan Wang, Beijing (CN)

(73) Assignee: Beijing FUNATE Innovation Technology Co., LTD., Beijing (CN)

( * ) Notice: Subject to any disclaimer, the term of this patent is extended or adjusted under 35 U.S.C. 154(b) by 0 days.

(21) Appl. No.: 16/739,203

(22) Filed: Jan. 10, 2020

(65) Prior Publication Data
US 2021/0106822 A1 Apr. 15, 2021

(30) Foreign Application Priority Data
Oct. 11, 2019 (CN) .......................... 201910965297.8

(51) Int. Cl.
*A45D 44/04* (2006.01)
*A61N 1/36* (2006.01)
*A61N 1/04* (2006.01)
*A45D 44/00* (2006.01)

(52) U.S. Cl.
CPC ......... *A61N 1/3603* (2017.08); *A45D 44/002* (2013.01); *A61N 1/0408* (2013.01)

(58) Field of Classification Search
CPC ... A61N 1/3603; A61N 1/0408; A45D 44/002
See application file for complete search history.

(56) References Cited

U.S. PATENT DOCUMENTS

| 5,527,357 A | * | 6/1996 | Springer, Jr. | ........ A61N 1/0452 607/140 |
| 2009/0085461 A1 | | 4/2009 | Feng et al. | |
| 2009/0153506 A1 | | 6/2009 | Liu et al. | |
| 2012/0045599 A1 | * | 2/2012 | Wei | ......................... B32B 37/14 428/35.7 |
| 2012/0250908 A1 | | 10/2012 | Jiang et al. | |
| 2013/0110215 A1 | | 5/2013 | Fan et al. | |
| 2019/0008721 A1 | * | 1/2019 | Hsu | ....................... A61N 1/0408 |

FOREIGN PATENT DOCUMENTS

| CN | 107260390 | | 10/2017 |
| CN | 107260390 A | * | 10/2017 |
| CN | 107616911 | | 1/2018 |
| CN | 207168836 | | 4/2018 |
| CN | 108159563 | | 6/2018 |
| CN | 208838309 | | 5/2019 |
| CN | 109984944 | | 7/2019 |
| CN | 209435460 U | | 9/2019 |

(Continued)

*Primary Examiner* — Ankit D Tejani
*Assistant Examiner* — Joshua Brendon Solomon
(74) *Attorney, Agent, or Firm* — ScienBiziP, P.C.

(57) ABSTRACT

A beauty instrument with mask includes a flexible mask and a controller. The flexible mask includes a first flexible layer, a second flexible layer, a plurality of functional layers located between the first flexible layer and the second flexible layer, and a plurality of electrodes electrically connected with the plurality of functional layers. The functional layer includes a carbon nanotube layer including a plurality of carbon nanotubes uniformly distributed. The flexible mask is electrically coupled with the controller via the plurality of electrodes.

20 Claims, 15 Drawing Sheets

(56) References Cited

FOREIGN PATENT DOCUMENTS

| | | |
|---|---|---|
| JP | 2009-146424 | 7/2009 |
| JP | 2010-18515 | 1/2010 |
| JP | 2012-130484 | 7/2012 |
| JP | 2014-146478 | 8/2014 |
| JP | 2015-47382 | 3/2015 |
| JP | 2017-108758 | 6/2017 |
| JP | 2018-187364 | 11/2018 |
| KR | 10-2004-0073928 | 8/2004 |
| WO | 2015145195 | 10/2015 |

* cited by examiner

BEAUTY INSTRUMENT WITH MASK

CROSS-REFERENCE TO RELATED APPLICATIONS

The application is also related to copending applications entitled, "METHOD FOR USING BEAUTY INSTRUMENT WITH MASK", filed Jan. 10, 2020 Ser. No. 16/739,206; "BEAUTY INSTRUMENT WITH MASK", filed Jan. 10, 2020 Ser. No. 16/739,210; "METHOD FOR USING BEAUTY INSTRUMENT WITH MASK", filed Jan. 10, 2020 Ser. No. 16/739,212; "SOFT PHYSIOTHERAPY INSTRUMENT AND METHOD FOR USING THE SAME", filed Jan 10, 2020 Ser. No. 16/739,224.

FIELD

The subject matter herein generally relates to a beauty instrument with mask.

BACKGROUND

As the living standards being improved, demands for beauty are becoming greater. As such, products of beauty flexible masks and beauty instruments are popular, especially the beauty instruments. Beauty instruments which can produce micro-currents to stimulate human faces are favored by consumers. Existing beauty instruments are hand-held beauty instruments and require users to operate the beauty instruments in front of a mirror. This makes the hand-held beauty instruments inconvenient to use.

BRIEF DESCRIPTION OF THE DRAWINGS

Implementations of the present technology will now be described, by way of embodiments, with reference to the attached figures, wherein.

DETAILED DESCRIPTION

Figure 1:
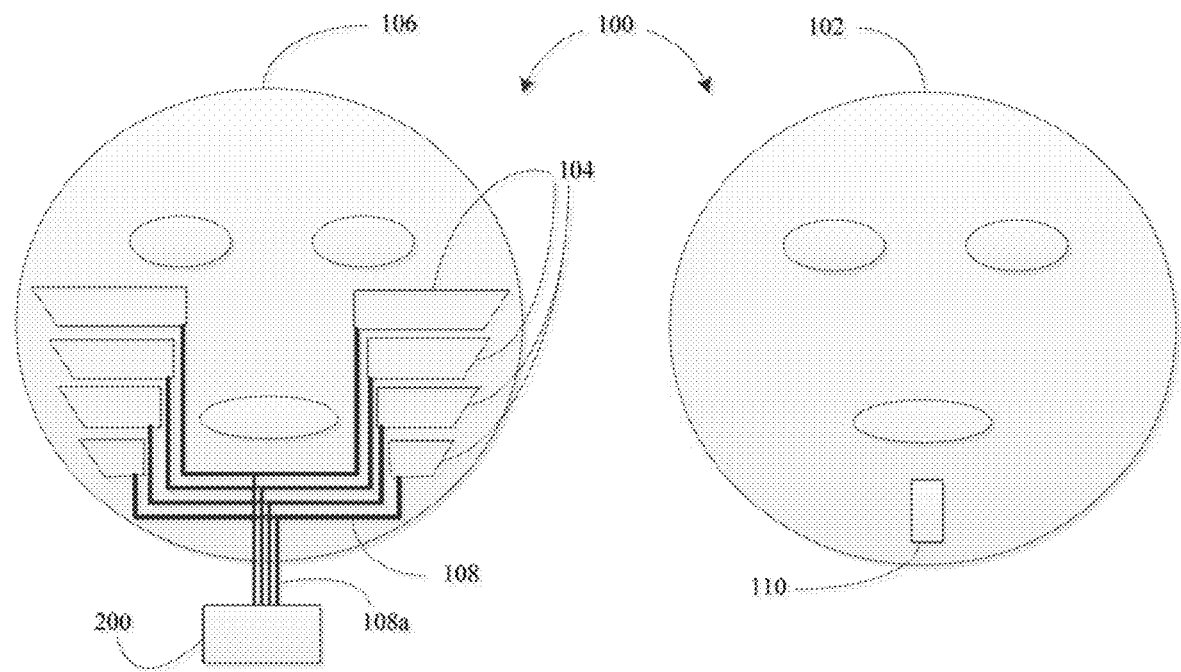
FIG. 1 is a schematic view of a beauty instrument with mask according to a first embodiment.

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean "at least one."

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "contact" is defined as a direct and physical contact. The term "substantially" is defined to be that while essentially conforming to the particular dimension, shape, or other feature that is described, the component is not or need not be exactly conforming to the description. The term "comprising," when utilized, means "including, but not necessarily limited to"; it specifically indicates open-ended inclusion or membership in the so-described combination, group, series, and the like.

Figure 2:
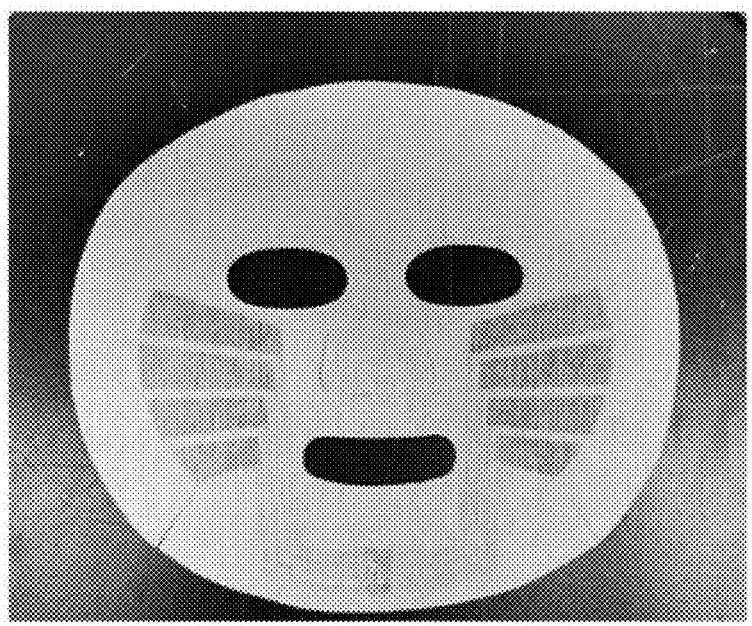
FIG. 2 is a photo of the beauty instrument with mask according to the first embodiment.
Figure 3:
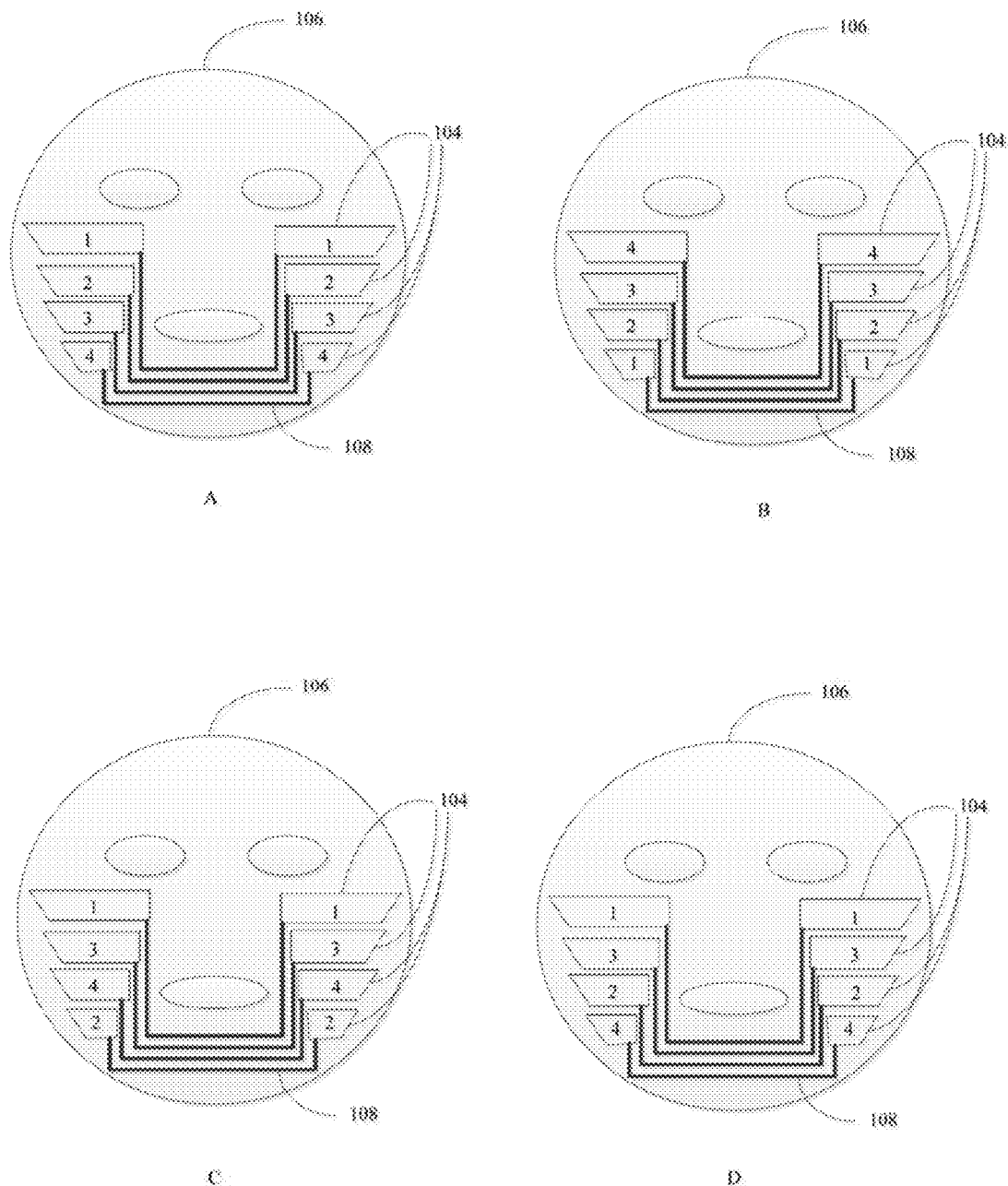
FIG. 3 shows schematic views of functional layers' numberings in the beauty instrument with mask provided by the first embodiment.

Referring to FIGS. 1 and 2, a beauty instrument with mask 10 according to a first embodiment is provided. The beauty instrument with mask 10 includes a flexible mask 100 and a controller 200 for controlling the flexible mask 100. The flexible mask 100 includes a first flexible layer 102 and a second flexible layer 106 overlapped with each other (for clarity of display, in FIG. 1, the first flexible layer 102 and the second flexible layer 106 are separately shown), the first flexible layer 102 and the second flexible layer 106 have corresponding eye and mouth openings (not labeled). The flexible mask 100 further includes a plurality of functional layers 104 sandwiched between the first flexible layer 102 and the second flexible layer 106, the plurality of functional layers 104 are symmetrically distributed or regularly distributed, and a plurality of electrodes 108, each of the plurality of electrodes 108 is electrically connected with a single functional layer 104 or a pair of functional layers 104. If a quantity of the plurality of electrodes 108 is defined as $K(K=1, 2, 3, 4, 5 \ldots)$, then a quantity of the plurality of functional layers 104 is $2K(K=1, 2, 3, 4, 5 \ldots)$ or K. The controller is electrically connected to the K electrodes 108, and the plurality of functional layers 104 in the flexible mask 100 are controlled by the K electrodes 108. In one embodiment, according to FIG. 1, the quantity of the plurality of functional layers 104 is 8 (2K), for example, the quantity of the plurality of electrodes 108 is 4 (K). Each electrode 108 is electrically connected with two functional layers 104. Two ends of the electrode 108 are separately connected with the two functional layers 104. The two functional layers 104 electrically connected with the electrode 108 are symmetrically located on two sides of a user's face. Each of the plurality of functional layers 104 is a carbon nanotube layer.

At least one functional layer 104 can be a plurality of functional layers 104, or one functional layer 104. As shown in FIG. 1, the flexible mask 100 includes 8 functional layers 104. The 8 functional layers 104 are symmetrically distributed at a cheek position of a human face. When the flexible mask 100 includes a plurality of functional layers 104, the position of the functional layer 104 is not limited, and can be a forehead position, a cheek position, an eye below position, a nose position, or the like. The number of the functional layers 104 is not limited and can be adjusted as needed, and may be 2, 8, 15, 20, or the like. An area of each functional layer 104 is not limited and can be adjusted as needed. Adjacent functional layers 104 are spaced apart and insulated from each other.

The controller 200 includes a plurality of function buttons for controlling the flexible mask 100. The controller 200 is electrically connected to the flexible mask 100 through the plurality of electrodes 108. The controller is used to input a voltage between two of the plurality of electrodes 108 to produce current in the plurality of functional layers 104. A circuit is formed between the controller, the two of the plurality of electrodes 108, the plurality of functional layers 104 electrically connected with the two of the plurality of electrodes 108, and the face skin of the user. As such, the current flows through the controller, the two of the plurality of electrodes 108, the plurality of functional layers 104 electrically connected with the two of the plurality of electrodes 108, and the face skin of the user. Each of the plurality of function buttons can control the current magnitude, the frequency of the current, the position of the input current, etc., to control the plurality of functional layers 104 inside the flexible mask 100. The flexible mask 100 can be movably coupled to the controller 200. Optionally, the first flexible layer 102 or the second flexible layer 106 can include a window 110, and the plurality of electrodes 108 a first electrode lead 114 and a second electrode lead 116 are exposed from the window 110 and electrically connected to the controller 200 via a plurality of lead wires 108a. The window 110 is provided with an access port through which the controller 200 is connected to the flexible mask 100. The flexible mask 100 can be replaced as needed. The flexible mask 100 can also be cleaned for reuse.

A material of the first flexible layer 102 or the second flexible layer 106 can be a flexible material such as nonwoven fabric, silk, flexible cloth, porous flexible paper, or silica gel, and can be directly attached to a person's face. A thickness of the first flexible layer 102 or the second flexible layer 106 can be set according to actual needs. In this embodiment, the thickness of the first flexible layer 102 or the second flexible layer 106 is in a range from 10 to 100 micrometers. In use of the beauty instrument with mask, the second flexible layer 106 will be directly attached on a face. The second flexible layer 106 has a porous structure.

A material of the electrode 108 can be metal, alloy, indium tin oxide (ITO), antimony tin oxide (ATO), conductive silver paste, conductive polymer, or conductive carbon nanotube. The metal or the alloy can be aluminum, copper, tungsten, molybdenum, gold, titanium, rhodium, palladium, iridium, or any alloy thereof. In this embodiment, the K electrodes 108 are all copper wires with a diameter of 1 micrometer. Preferably, an insulating layer can be coated on the surface of each of the K electrodes 108. A material of the insulating layer can be a flexible material.

Each electrode 108 corresponds to one functional layer 104 or two functional layers 104. When one electrode 108 corresponds to one functional layer 104, one end of the electrode 108 is electrically connected to the functional layer 104, and the other end is electrically connected to the controller. In this case, the controller can control the one functional layer 104 through the one electrode 108. The numbering of the one electrode 108 corresponds to the numbering of the one functional layer 104. When one electrode 108 corresponds to two functional layers 104, two ends of the electrode 108 are separately electrically connected to one of the two functional layers 104, and a middle part of the electrode 108 is electrically connected to the controller. In this case, the controller can control the two functional layers 104 simultaneously, and the numbering of the one electrode 108 corresponds to the numbering of a pair of functional layers 104. The two functional layers 104 electrically connected with the same electrode 108 have the same numbering. The numbering order of the plurality of electrodes 108 does not represent the position order. That is, the positions of two electrodes 108 with neighbor numbering may be adjacently or at intervals. Since the numbering of the electrode 108 corresponds to the numbering of the functional layer 104, it can be understood that the positions of two pairs of adjacent functional layers 104 or the two adjacent functional layers 104 with neighbor numbering may be adjacently or at intervals. Referring to FIG. 1, in this embodiment, one electrode 108 corresponds to a pair of functional layers 104, and the flexible mask 100 includes four pairs of functional layers 104. Referring to FIGS. 3A to 3D, for example, the four pairs of functional layers 104 are numbered 1, 2, 3, and 4, positions 1, 2, 3, and 4 can be arbitrarily set.

The carbon nanotube layer includes a plurality of carbon nanotubes joined by van der Waals attractive force therebetween. The carbon nanotube layer can be a substantially pure structure of carbon nanotubes, with few impurities. The carbon nanotube layer can be a freestanding structure, that is, the carbon nanotube layer can be supported by itself without a substrate. For example, if at least one point of the carbon nanotube layer is held, the entire carbon nanotube layer can be lifted while remaining its structural integrity.

The carbon nanotubes in the carbon nanotube layer can be orderly or disorderly arranged. The term 'disordered carbon nanotube layer' refers to a structure where the carbon nanotubes are arranged along different directions, and the aligning directions of the carbon nanotubes are random. The number of the carbon nanotubes arranged along each different direction can be almost the same (e.g. uniformly disordered). The disordered carbon nanotube layer can be isotropic, namely the carbon nanotube layer has properties identical in all directions of the carbon nanotube layer. The carbon nanotubes in the disordered carbon nanotube layer can be entangled with each other.

The carbon nanotube layer including ordered carbon nanotubes is an ordered carbon nanotube layer. The term 'ordered carbon nanotube layer' refers to a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions). The carbon nanotubes in the carbon nanotube layer can be selected from single-walled, double-walled, and/or multi-walled carbon nanotubes. The carbon nanotube layer may include at least one carbon nanotube film. In other embodiments, the carbon nanotube layer is composed of one carbon nanotube film or at least two carbon nanotube films. In other embodiment, the carbon nanotube layer consists one carbon nanotube film or at least two carbon nanotube films.

Figure 4:
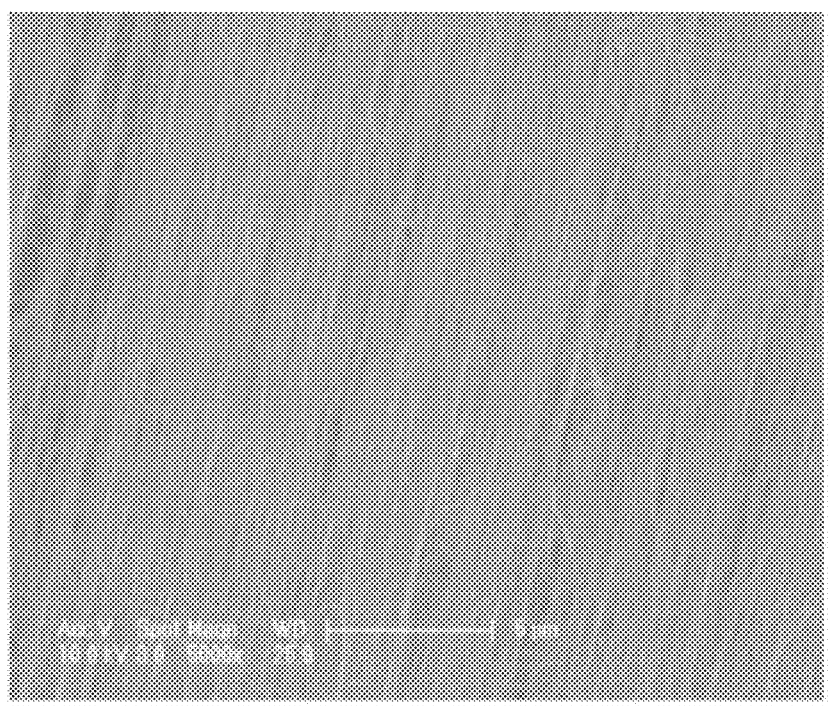
FIG. 4 shows a Scanning Electron Microscope (SEM) image of a drawn carbon nanotube film.
Figure 5:
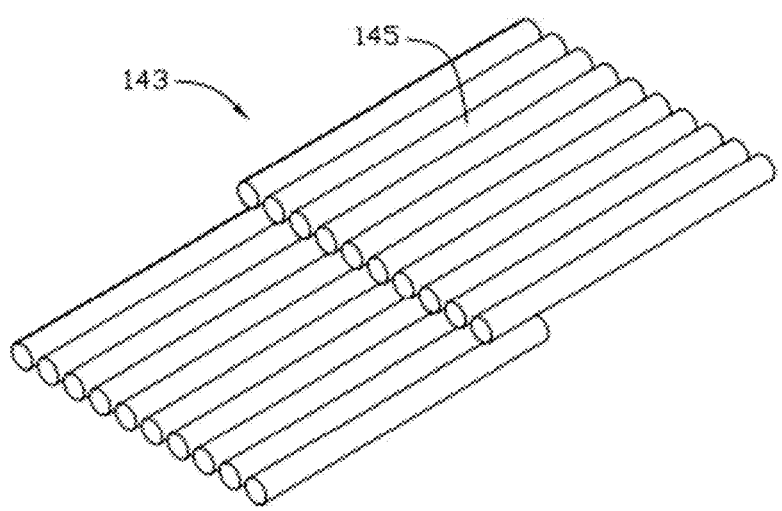
FIG. 5 is a schematic view of carbon nanotube segments in the drawn carbon nanotube film.

In one embodiment, the carbon nanotube film can be a drawn carbon nanotube film. Referring to FIG. 4, the drawn carbon nanotube film includes a number of successive and oriented carbon nanotubes joined end-to-end by van der Waals attractive force therebetween. The drawn carbon nanotube film is a freestanding film. Each drawn carbon nanotube film includes a number of successively oriented carbon nanotube segments joined end-to-end by van der Waals attractive force therebetween. Referring to FIG. 5, each carbon nanotube segment 143 includes a number of carbon nanotubes 145 substantially parallel to each other, and joined by van der Waals attractive force therebetween. Some variations can occur in the drawn carbon nanotube film. The carbon nanotubes in the drawn carbon nanotube film are oriented along a preferred orientation. The drawn carbon nanotube film can be treated with an organic solvent to increase mechanical strength and toughness of the drawn carbon nanotube film and reduce coefficient of friction of the drawn carbon nanotube film. A thickness of the drawn carbon nanotube film may range from about 0.5 nanometers to about 100 micrometers. The drawn carbon nanotube film can be used as a carbon nanotube layer directly.

The carbon nanotubes in the drawn carbon nanotube film can be single-walled, double-walled, and/or multi-walled carbon nanotubes. The diameters of the single-walled carbon nanotubes may range from about 0.5 nanometers to about 50 nanometers. The diameters of the double-walled carbon nanotubes may range from about 1 nanometer to about 50 nanometers. The diameters of the multi-walled carbon nanotubes may range from about 1.5 nanometers to about 50 nanometers. The lengths of the carbon nanotubes may range from about 200 micrometers to about 900 micrometers.

The carbon nanotube layer may include at least two stacked drawn carbon nanotube films. The carbon nanotubes in the drawn carbon nanotube film are aligned along one preferred orientation, an angle can exist between the orientations of carbon nanotubes in adjacent drawn carbon nanotube films, whether stacked or adjacent. An angle between the aligned directions of the carbon nanotubes in two adjacent drawn carbon nanotube films may range from about 0 degrees to about 90 degrees (e.g. about 15 degrees, 45 degrees, or 60 degrees).

Figure 6:
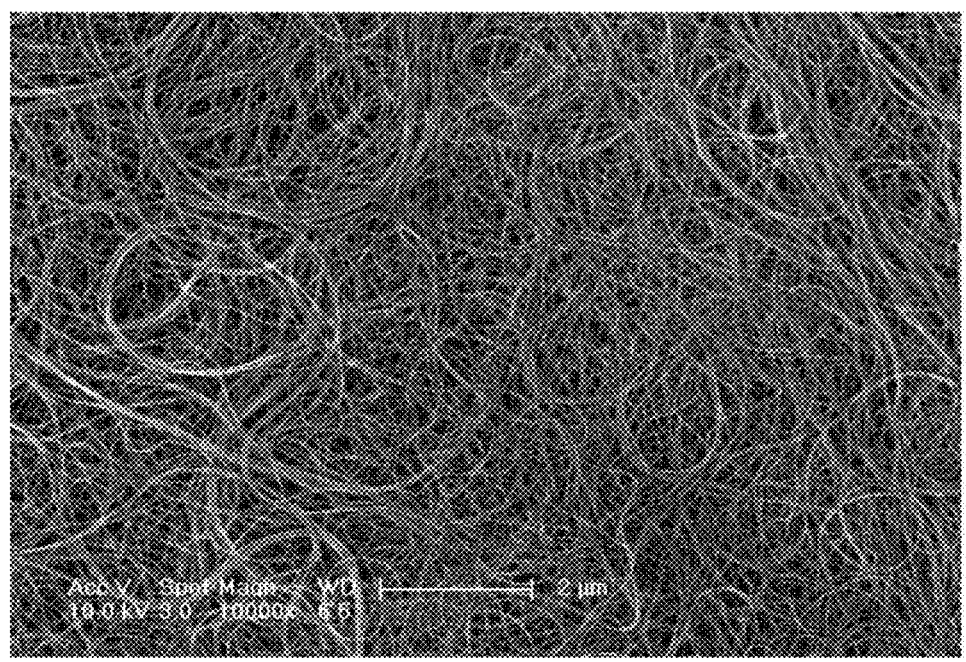
FIG. 6 shows an SEM image of a flocculated carbon nanotube film.

In other embodiments, the carbon nanotube film can be a flocculated carbon nanotube film. Referring to FIG. 6, the flocculated carbon nanotube film may include a plurality of long, curved, and disordered carbon nanotubes entangled with each other. Furthermore, the flocculated carbon nanotube film can be isotropic. The carbon nanotubes can be substantially uniformly dispersed in the flocculated carbon nanotube film. Adjacent carbon nanotubes are acted upon by van der Waals attractive force to obtain an entangled structure with micropores defined therein. Because the carbon nanotubes in the flocculated carbon nanotube film are entangled with each other, the carbon nanotube layer employing the flocculated carbon nanotube film has excellent durability, and can be fashioned into desired shapes with a low risk to the integrity of the carbon nanotube layer. A thickness of the flocculated carbon nanotube film may range from about 0.5 nanometers to about 1 millimeter.

Figure 7:
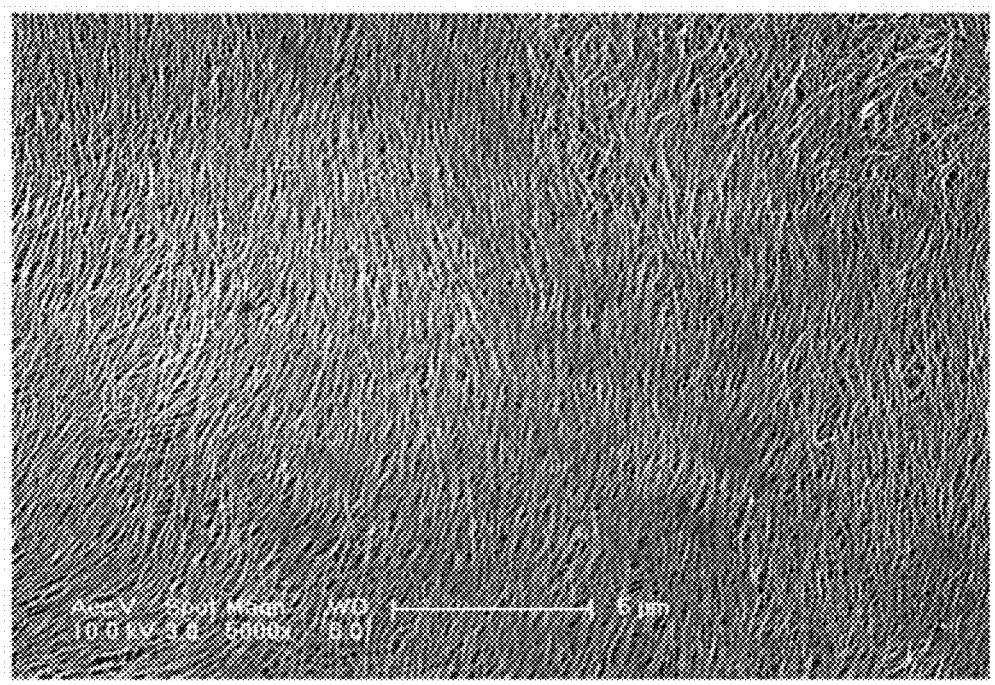
FIG. 7 shows an SEM image of a pressed carbon nanotube film.

Referring to FIG. 7, in other embodiments, the carbon nanotube film can be a pressed carbon nanotube film. The pressed carbon nanotube film is formed by pressing a carbon nanotube array. The carbon nanotubes in the pressed carbon nanotube film are arranged along a same direction or along different directions. The carbon nanotubes in the pressed carbon nanotube film can rest upon each other. Adjacent carbon nanotubes are attracted to each other and are joined by van der Waals attractive force. An angle between a primary alignment direction of the carbon nanotubes and a surface of the pressed carbon nanotube film is in a range from 0 degrees to 15 degrees. The greater the pressure applied, the smaller the angle obtained. In one embodiment, the carbon nanotubes in the pressed carbon nanotube film are arranged along different directions, the carbon nanotube layer can be isotropic. A thickness of the pressed carbon nanotube film may range from about 0.5 nanometers to about 1 millimeter.

Figure 8:
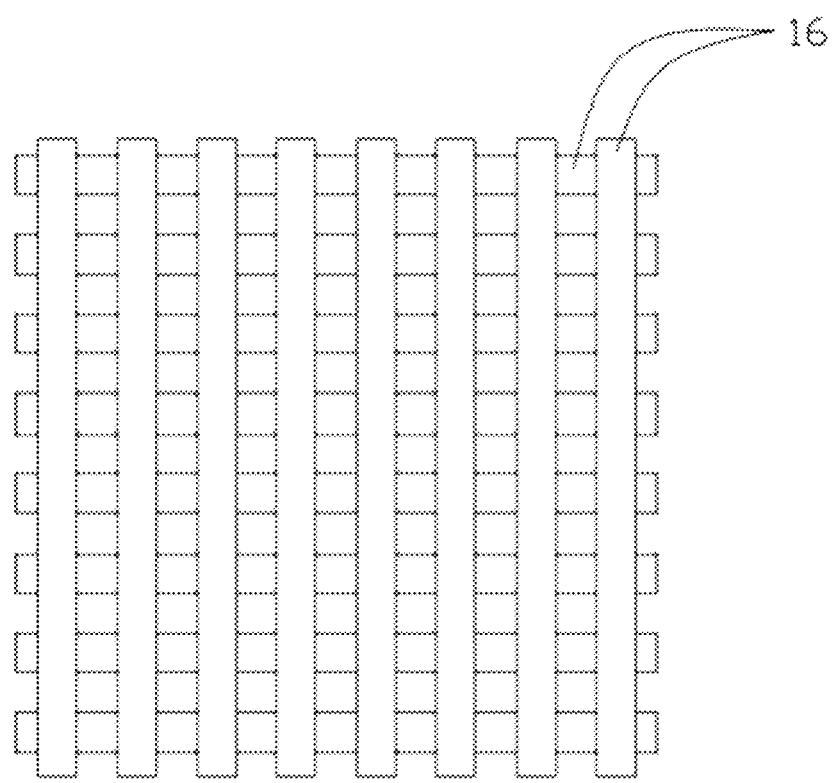
FIG. 8 is a schematic view of a functional layer including a plurality of carbon nanotube wires crossed with each other.
Figure 9:
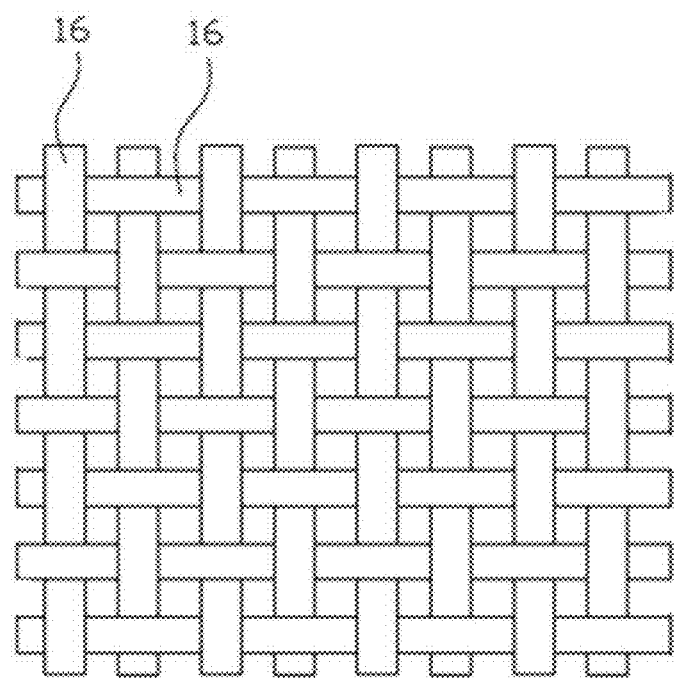
FIG. 9 is a schematic view of a functional layer including a plurality of carbon nanotube wires weaved with each other.
Figure 10:
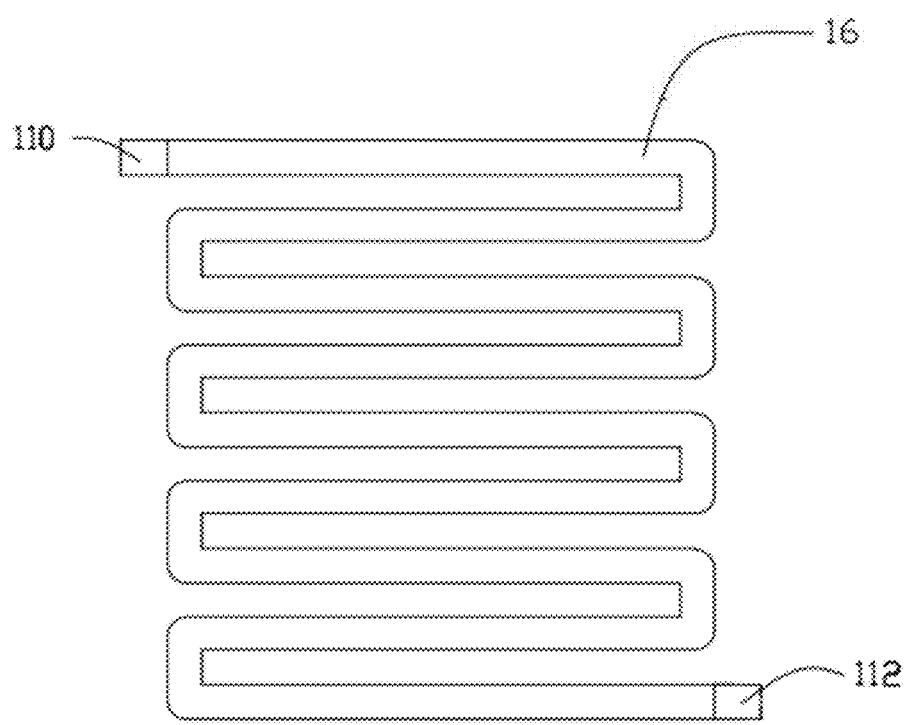
FIG. 10 is a schematic view of a functional layer including a bended and winded carbon nanotube wire.

In some embodiments, the carbon nanotube layer may include a plurality of carbon nanotube wires. Referring to FIG. 8, a plurality of carbon nanotube wires 16 can be crossed with each other to form the carbon nanotube layer. Referring to FIG. 9, a plurality of carbon nanotube wires 16 can be waved with each other to form the carbon nanotube layer. In other embodiments, the carbon nanotube layer may include only one carbon nanotube wire. Referring to FIG. 10, one carbon nanotube wire 16 can be bended to form the carbon nanotube layer.

Figure 11:
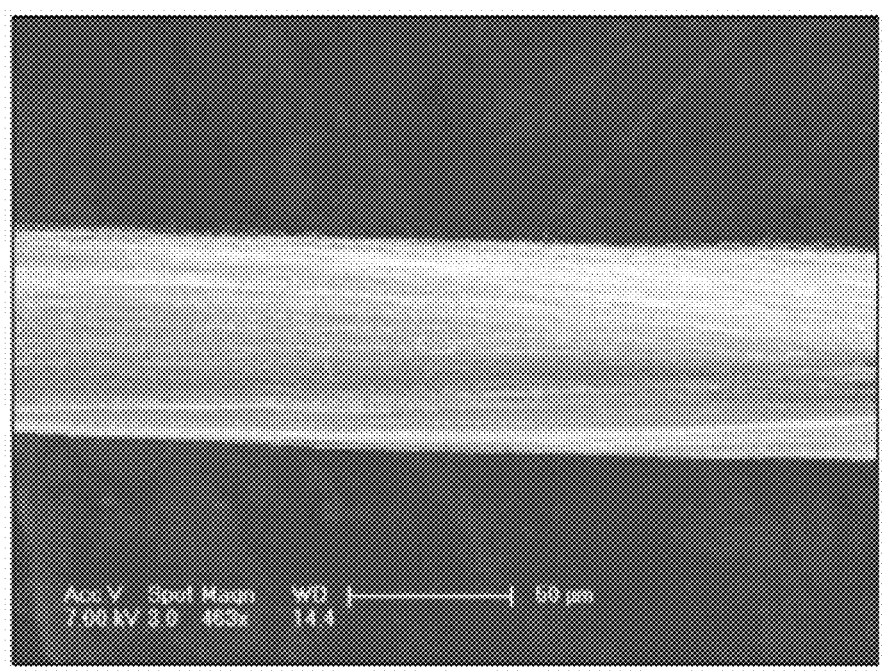
FIG. 11 is an SEM image of an untwisted carbon nanotube wire.

The carbon nanotube wire can be untwisted or twisted. Referring to FIG. 11, an untwisted carbon nanotube wire includes a plurality of carbon nanotubes substantially oriented along a same direction (i.e., a direction along the length direction of the untwisted carbon nanotube wire). The untwisted carbon nanotube wire can be a pure structure of carbon nanotubes. The untwisted carbon nanotube wire can be a freestanding structure. The carbon nanotubes are substantially parallel to the axis of the untwisted carbon nanotube wire. In one embodiment, the untwisted carbon nanotube wire may include a plurality of successive carbon nanotube segments joined end to end by van der Waals attractive force therebetween. Each carbon nanotube segment may include a plurality of carbon nanotubes substantially parallel to each other, and combined by van der Waals attractive force therebetween. The carbon nanotube segments can vary in width, thickness, uniformity, and shape. The length of the untwisted carbon nanotube wire can be arbitrarily set as desired. A diameter of the untwisted carbon nanotube wire may range from about 50 nanometers to about 100 micrometers.

Figure 12:
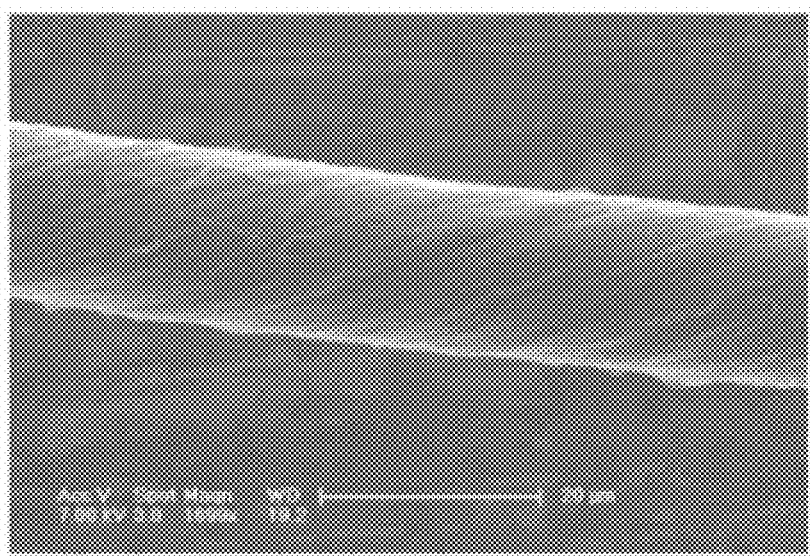
FIG. 12 is an SEM image of a twisted carbon nanotube wire.

Referring to FIG. 12, a twisted carbon nanotube wire may include a plurality of carbon nanotubes helically oriented around an axial direction of the twisted carbon nanotube wire. The twisted carbon nanotube wire can be a pure structure of carbon nanotubes. The twisted carbon nanotube wire can be a freestanding structure. In one embodiment, the twisted carbon nanotube wire may include a plurality of successive carbon nanotube segments joined end to end by van der Waals attractive force therebetween. Each carbon nanotube segment may include a plurality of carbon nanotubes substantially parallel to each other, and combined by van der Waals attractive force therebetween. The length of the carbon nanotube wire can be set as desired. A diameter of the twisted carbon nanotube wire may range from about 50 nanometers to about 100 micrometers. Furthermore, the twisted carbon nanotube wire can be treated with a volatile organic solvent after being twisted. After being soaked by the organic solvent, the adjacent substantially parallel carbon nanotubes in the twisted carbon nanotube wire will bundle together, due to a surface tension of the organic solvent when the organic solvent volatilizes. The density and strength of the twisted carbon nanotube wire will increase.

The carbon nanotube layer has a better flexibility than the first flexible layer 102 and/or the second flexible layer 106. When the carbon nanotube layer is used as the functional layer 104 in the flexible mask 100, the flexibility of the entire flexible mask 100 is not decreased by the functional layer 104. The carbon nanotube layer has a large strength, as such, no matter how the flexible mask 100 is bent or pulled, and the carbon nanotube layer is not damaged.

Figure 13:
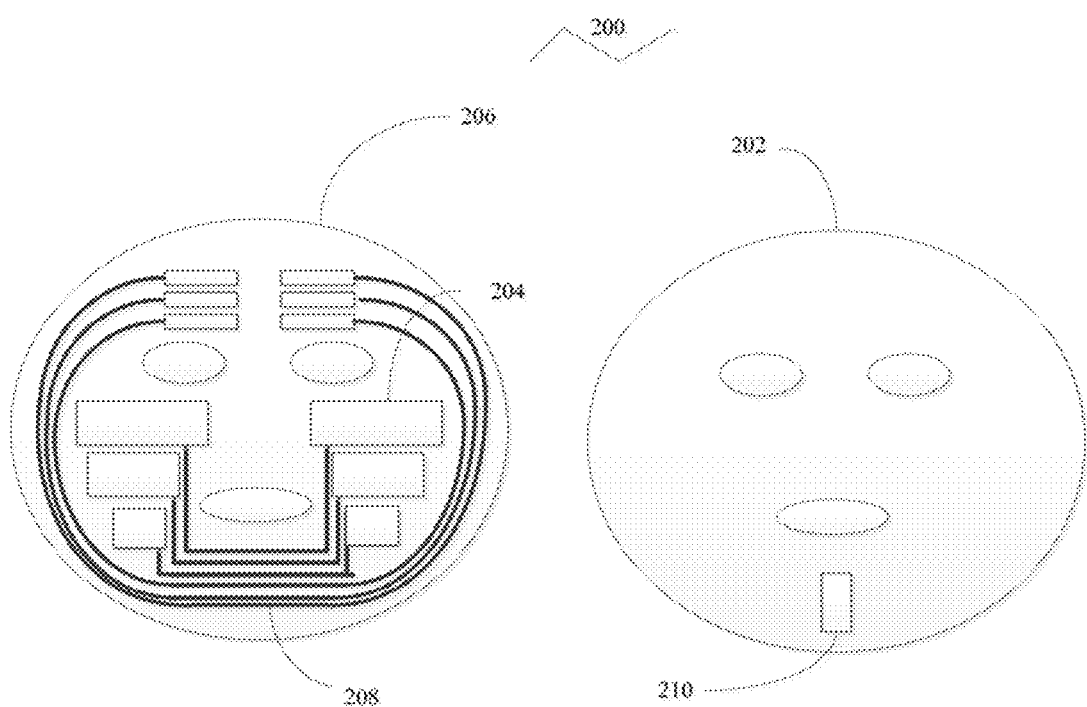
FIG. 13 is a schematic view of a beauty instrument with mask according to a second embodiment.

A beauty instrument with mask according to a second embodiment is provided. The beauty instrument with mask comprises a flexible mask and a controller. Referring to FIG. 13, a flexible mask 200 includes a first flexible layer 202 and a second flexible layer 206, the first flexible layer 202 and the second flexible layer 206 are stacked with each other. The flexible mask 200 further includes a plurality of functional layers 204 sandwiched between the first flexible layer 202 and the second flexible layer 206 and a plurality of electrodes 208 electrically connected with the plurality of functional layers 204. In this embodiment, a quantity of the plurality of functional layers 204 is 12, and a quantity of the plurality of electrodes 208 is 6. Each of the plurality of electrodes 208 is electrically connected with a pair of functional layers 204. As shown in FIG. 13, there are 6 functional layers 204 symmetrically located on a cheek position, and 6 functional layers 204 symmetrically located on a forehead position.

Other characteristics of the beauty instrument with mask in the second embodiment are the same as that of the beauty instrument with mask in the first embodiment.

Figure 14:
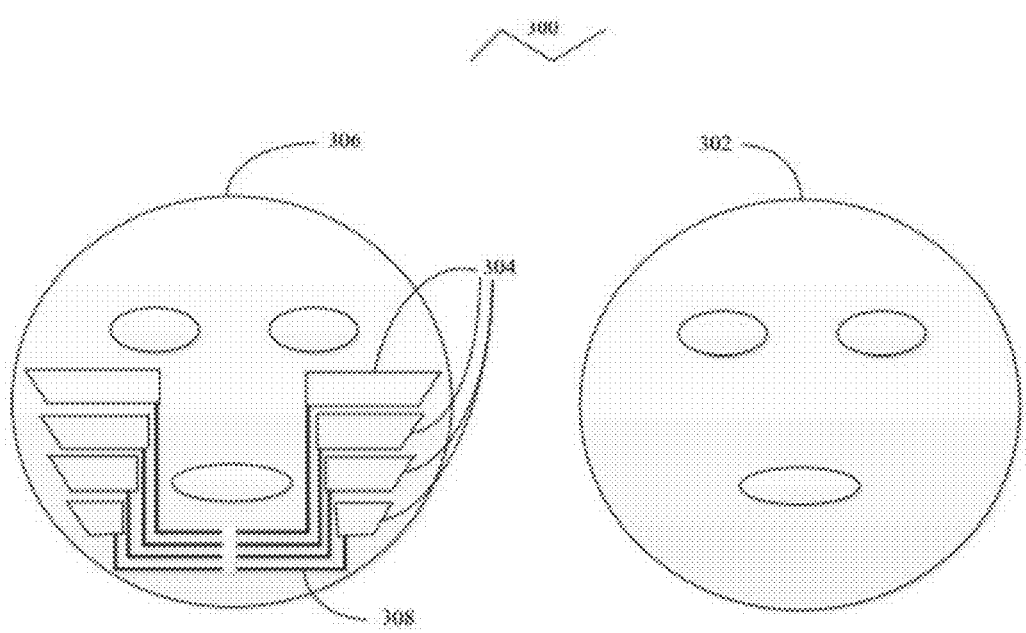
FIG. 14 is a schematic view of part of a beauty instrument with mask according to a third embodiment.

A beauty instrument with mask according to a third embodiment is provided. The beauty instrument with mask comprises a flexible mask and a controller. Referring to FIG. 14, a flexible mask 300 includes a first flexible layer 302 and a second flexible layer 306, the first flexible layer 302 and the second flexible layer 306 are stacked with each other. The flexible mask 300 further includes a plurality of functional layers 304 sandwiched between the first flexible layer 302 and the second flexible layer 306 and a plurality of electrodes 308 electrically connected with the plurality of functional layers 304. In this embodiment, each of the plurality of electrodes 308 is electrically connected with a single functional layer 304. As shown in FIG. 14, there are 8 functional layers 304 symmetrically located on a cheek position, and 8 electrodes 308 are electrically connected with the 8 functional layers 304 in a one by one manner.

Other characteristics of the beauty instrument with mask in the third embodiment are the same as that of the beauty instrument with mask in the first embodiment.

Figure 15:
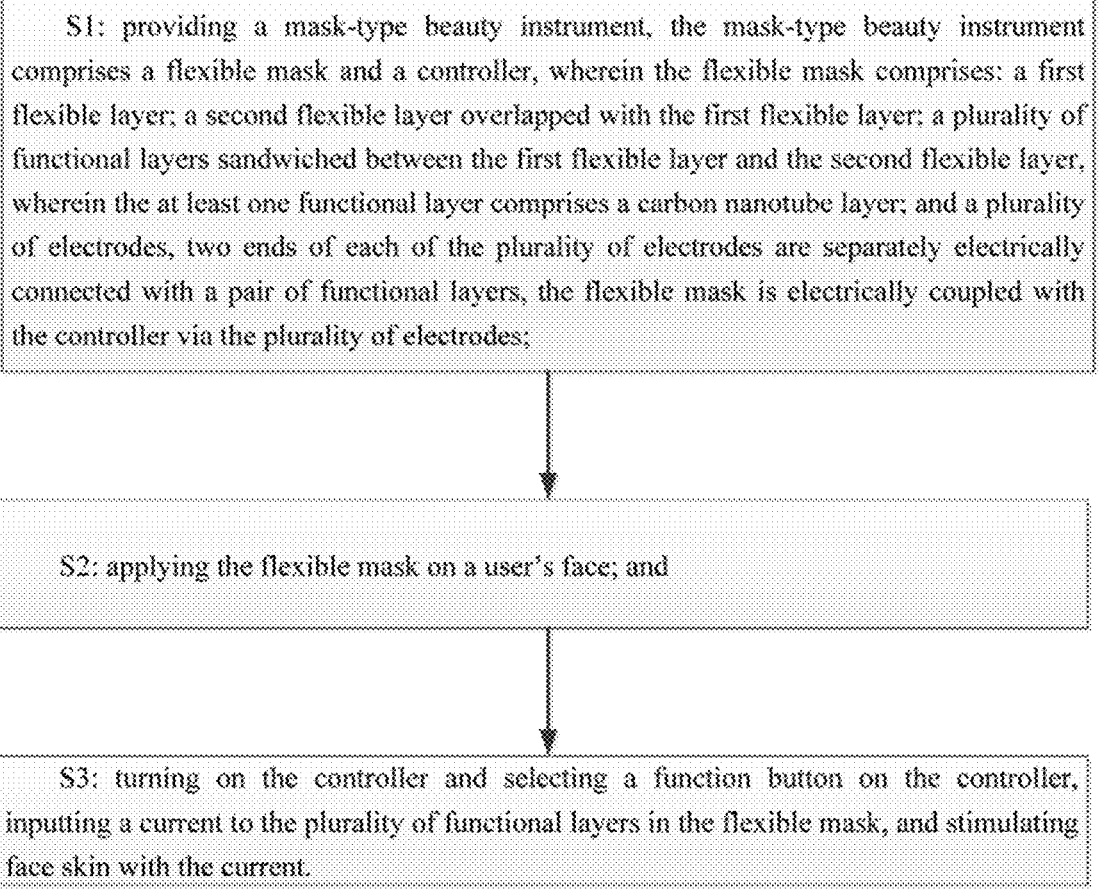
FIG. 15 is a flow chart according to one embodiment showing a method for using a beauty instrument with mask.

Referring to FIG. 15, the present disclosure further provides a method of using a beauty instrument with mask, the method comprises the steps of:

Step S1: providing a beauty instrument with mask, the beauty instrument with mask comprises a flexible mask and a controller;

Step S2: applying the flexible mask on a user's face; and

Step S3: turning on the controller and selecting a function button on the controller, inputting a current to a plurality of functional layer in the flexible mask, and stimulating face skin with the current.

In step S1, the beauty instrument with mask is any one of the beauty instrument with masks discussed above.

Alternatively, before step S2, the flexible mask can be further infiltrated with a liquid, that is, before the flexible mask of the beauty instrument with mask is applied on the user's face. The liquid can be a cosmetic liquid.

In step S3, the controller includes a plurality of function buttons for controlling the flexible mask. Each of the plurality of function buttons is used to control the functional layer inside the flexible mask to achieve the stimulating function. Each of the plurality of function buttons can be configured to control a current magnitude, a current frequency, a position of the functional layer which the current is input. The controller can input current to at least two functional layers via two electrodes. As such, the controller can control the functional layer inside the flexible mask to simultaneously stimulate the face skin, or selectively control a certain functional layer or some certain functional layers to simultaneously stimulate the face skin. For example, when the functional layers are located at a forehead position, a cheek position, and a chin position, the controller can control the functional layers in the above positions to circulate stimulate the face skin in the order of the forehead position, the cheek position, and the chin position.

In use of the beauty instrument with mask, a voltage is applied to two pairs of functional layers or two functional layers via two electrodes, and a micro-current will be input through the two electrode to the two pairs of functional layers or the two functional layers, and face skin between or under the two pairs of functional layers or the two functional layers will be stimulated by the micro-current. The voltage applied on each two electrodes can be kept for a power-on time, and the voltage is stop for a dwell time, then the voltage is applied to another two electrodes for another power-on time. The voltage can be applied to two electrodes in an order 1 and 2, 2 and 3, 3 and 4 . . . K−1 and K(K is the numbering of each electrode), so that the two pairs of functional layers corresponding to each two electrodes are cyclically input current, and the face skin corresponding the two pairs of functional layers are cyclically stimulated. The numbers of the two pairs of functional layers are adjacent, such as numbers 2 and 3, which does not mean that the positions of the two pairs of functional layers are adjacent. The positions of the two pairs of functional layers adjacent to each other can be arbitrarily set according to actual needs. Referring to FIG. 3A to FIG. 3D, in these embodiments, each electrode 108 corresponds to a pair of functional layers 104, and the flexible mask 100 includes four pairs of functional layers 104. The four electrodes 108 are numbered 1, 2, 3, and 4, and the four pairs of functional layers 104 are numbered 1, 2, 3, and 4. Positions 1, 2, 3, and 4 can be arbitrarily set, for example, 3A to 3D in FIG. 3. In the application, the electrodes 108 are energized according to the circulation pattern of the electrodes numbered 1 and 2, 2 and 3, and 3 and 4, thereby sequentially or selectively generating micro-currents in the two pairs of functional layers, which in turn stimulate the face skin.

In one embodiment according to FIG. 3B, in use of the beauty instrument with mask, the electrodes 108 are energized according to the circulation pattern of the electrodes numbered 1 and 2, 2 and 3, and 3 and 4, thereby sequentially or selectively generating micro-currents in the two pairs of functional layers, which in turn stimulate the face skin. In this embodiment, the power-on time of each pair of electrodes 108 is 1 s and the dwell time is 1 s. That is, with a cycle of 2 s, the power is first applied for 1 s, and then stopped for 1 s, and this cycle is performed. Among them, the voltage applied on each two electrodes is in a range of 20V-36V and the frequency of the voltage is 90 Khz.

The flexible mask can be movably coupled to the controller. The flexible mask defines an access at the window position on the first flexible layer or the second flexible layer, and the controller is connected to the flexible mask through the access. The flexible mask can be changed as needed. The flexible mask can also be cleaned to achieve re-use purpose.

Compared with the prior art, the beauty instrument with mask provided by the present invention has the following advantages: first, it can directly fit on a user's face without the need to hold it by hand, which frees the user's hands. Secondly, through controlling a circuit by the controller, the skin on the user's face can be selectively stimulated, and the face parts to be stimulated can be selected more accurately without causing facial asymmetry. Third, the carbon nanotube layer is used as the functional layer, the carbon nanotube layer has a better flexibility than the first flexible layer or/and the second flexible layer, and the flexibility of the entire flexible mask will not be reduced due to the setting of the functional layers, the flexible mask can fit on the user's face well, and the user has a high comfort degree. Fourth, the carbon nanotube layer is used as a functional layer, a strength of the carbon nanotube layer is relatively large, no matter how to bend and pull or clean the flexible mask, the carbon nanotube layer will not be damaged, and the flexible mask has a long life.

Depending on the embodiment, certain blocks/steps of the methods described may be removed, others may be added, and the sequence of blocks may be altered. It is also to be understood that the description and the claims drawn to a method may comprise some indication in reference to certain blocks/steps. However, the indication used is only to be viewed for identification purposes and not as a suggestion as to an order for the blocks/steps.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A beauty instrument with mask, comprising:
a flexible mask and a controller configured to control the flexible mask, the flexible mask comprises:
a first flexible layer;
a second flexible layer overlapped with the first flexible layer;
a plurality of functional layers sandwiched between the first flexible layer and the second flexible layer, wherein each of the plurality of functional layers comprises a carbon nanotube layer, the carbon nanotube layer comprises a plurality of carbon nanotubes uniformly distributed in the carbon nanotube layer; and
a plurality of electrodes, wherein two ends of each of the plurality of electrodes are separately electrically connected with a pair of the plurality of functional layers, the flexible mask is electrically coupled with the controller via the plurality of electrodes.

2. The beauty instrument with mask of claim 1, wherein the first flexible layer or the second flexible layer defines a window, and the plurality of electrodes are exposed from the window and electrically connected to the controller.

3. The beauty instrument with mask of claim 1, wherein a material of the first flexible layer or the second flexible layer is non-woven fabric, silk, flexible cloth, porous flexible paper, or silica gel.

4. The beauty instrument with mask of claim 1, wherein the carbon nanotube layer comprises a carbon nanotube film or a plurality of carbon nanotube films overlapped with each other.

5. The beauty instrument with mask of claim 4, wherein the carbon nanotube film is a freestanding film.

6. The beauty instrument with mask of claim 5, wherein the carbon nanotube film comprises a plurality of successive and oriented carbon nanotubes joined end-to-end by van der Waals attractive force therebetween.

7. The beauty instrument with mask of claim 6, wherein the carbon nanotube film comprises a plurality of successively oriented carbon nanotube segments joined end-to-end by van der Waals attractive force therebetween, and each carbon nanotube segment comprises a plurality of carbon nanotubes substantially parallel to each other, and joined by van der Waals attractive force therebetween.

8. The beauty instrument with mask of claim 5, wherein the carbon nanotube film comprises a plurality of carbon nanotubes entangled with each other.

9. The beauty instrument with mask of claim 5, wherein the carbon nanotube film comprises a plurality of carbon nanotubes joined by van der Waals attractive force, an angle between a primary alignment direction of the carbon nanotubes and a surface of the carbon nanotube film is ranged from 0 degrees to 15 degrees.

10. The beauty instrument with mask of claim 1, wherein the carbon nanotube layer comprises at least one carbon nanotube wire, the at least one carbon nanotube wire comprises a plurality of successive carbon nanotube segments joined end to end by van der Waals attractive force therebetween and oriented along a length direction of the at least one carbon nanotube wire.

11. The beauty instrument with mask of claim 10, wherein the carbon nanotube layer comprises one carbon nanotube wire, the carbon nanotube wire is bended to form the carbon nanotube layer.

12. The beauty instrument with mask of claim 10, wherein the carbon nanotube layer comprises a plurality of carbon nanotube wires crossed or weaved with each other.

13. The beauty instrument with mask of claim 1, wherein a material of the plurality of at electrodes is metal, alloy, indium tin oxide (ITO), antimony tin oxide (ATO), conductive silver paste, conductive polymer or conductive carbon nanotube.

14. The beauty instrument with mask of claim 1, wherein a middle part of each of the plurality of electrodes is electrically connected to the controller.

15. The beauty instrument with mask of claim 1, wherein the plurality of functional layers is located at a forehead position, a cheek position, an eye below position, or a nose position.

16. The beauty instrument with mask of claim 1, wherein a circuit is formed by the controller, two of the plurality of electrodes, one of a plurality of functional layers electrically connected with the two of the plurality of electrodes, and face skin of the user.

17. A beauty instrument with mask, comprising:
a flexible mask and a controller configured to control the flexible mask, the flexible mask comprises:
a first flexible layer;
a second flexible layer overlapped with the first flexible layer;

a plurality of functional layers sandwiched between the first flexible layer and the second flexible layer, wherein each of the plurality of functional layers comprises a carbon nanotube layer, the carbon nanotube layer comprises a plurality of carbon nanotubes uniformly distributed in the carbon nanotube layer; and a plurality of electrodes, wherein one end of each of the plurality of electrodes is electrically connected with one of the plurality of functional layers, another end of each of the plurality of electrodes on the flexible mask is electrically coupled with the controller.

18. The beauty instrument with mask of claim 17, wherein the first flexible layer or the second flexible layer defines a window, and the plurality of electrodes are exposed from the window and electrically connected to the controller.

19. The beauty instrument with mask of claim 17, wherein a material of the first flexible layer or the second flexible layer is non-woven fabric, silk, flexible cloth, porous flexible paper, or silica gel.

20. The beauty instrument with mask of claim 17, wherein the carbon nanotube layer comprises a carbon nanotube film or a plurality of carbon nanotube films overlapped with each other.

* * * * *